United States Patent
Al Ghatta

(10) Patent No.: US 6,562,877 B2
(45) Date of Patent: May 13, 2003

(54) RECOVERY OF DICARBOXYLIC AROMATIC ACIDS FROM POLYESTER-RESIN CONTAINED IN ARTICLES FOR RECYCLING

(75) Inventor: Hussain Al Ghatta, Fiuggi (IT)

(73) Assignee: Sinco Ricerche S.p.A. (IT)

( * ) Notice: Subject to any disclaimer, the term of this patent is extended or adjusted under 35 U.S.C. 154(b) by 0 days.

(21) Appl. No.: 10/016,545

(22) Filed: Dec. 11, 2001

(65) Prior Publication Data

US 2002/0077500 A1 Jun. 20, 2002

(30) Foreign Application Priority Data

Dec. 15, 2000 (IT) .......................................... MI00A2721

(51) Int. Cl.$^7$ ............................ C08J 11/04; C07C 51/09
(52) U.S. Cl. ......................................... 521/48; 562/483
(58) Field of Search ............................ 521/48; 562/480, 562/483

(56) References Cited

U.S. PATENT DOCUMENTS

| | | | | |
|---|---|---|---|---|
| 3,703,488 A | * | 11/1972 | Morton | 260/2.3 |
| 3,937,671 A | * | 2/1976 | Gruntfest et al. | 260/2.3 |
| 4,355,175 A | * | 10/1982 | Pusztaszeri | 562/483 |
| 5,414,113 A | | 5/1995 | Broeker et al. | 562/413 |
| 6,103,930 A | | 8/2000 | Samuels et al. | 562/483 |

OTHER PUBLICATIONS

Webster's II New Riverside University Dictionary. pp. 176 and 484. Houghton Mifflin Co. (1994).*

* cited by examiner

*Primary Examiner*—Mukund J. Shah
*Assistant Examiner*—Zachary C. Tucker
(74) *Attorney, Agent, or Firm*—Cook, Alex, McFarron, Manzo, Cummings & Mehler, Ltd.

(57) ABSTRACT

A method for the recovery of dicarboxylic aromatic acids, in particular terephthalic acid, from manufactured aromatic polyester-resin articles for recycling, wherein the article, fragmented into chip form, is reacted in solution in a carboxylic acid with 2–6 carbon atoms and with a pKa from 4 to 6, preferably glacial acetic acid, in the presence of catalytic quantities of a strong acid with a pKa of less than 1, preferably aqueous hydrochloric acid or sulfuric acid, operating at temperatures from 160° to 250° C.

24 Claims, No Drawings

RECOVERY OF DICARBOXYLIC AROMATIC ACIDS FROM POLYESTER-RESIN CONTAINED IN ARTICLES FOR RECYCLING

DESCRIPTION

The present invention relates to a method of recovering dicarboxylic aromatic acids from manufactured articles for recycling made of or containing aromatic polyester resins, such as beverage bottles, fibres and films, or from waste from the processing of these resins.

In particular, the invention relates to the recovery of terephthalic acid from bottles for recycling which are made of PET, polyethyl naphthenates (PEN) or ethylene terephthalic copolymers in which some of the terephthalic acid units are replaced by units derived from isophthalic acid and/of 2,6-naphthalene dicarboxylic acid.

DESCRIPTION OF THE PRIOR ART

Methods are known for recovering dicarboxylic aromatic acids, in particular, terephthalic acid and 2,6-naphthalene dicarboxylic acid, from manufactured articles for recycling which are made of aromatic polyester resins, in which the resin of the article, suitably reduced to chips or fragments, is depolymerized by hydrolysis with water at high temperature (200–300° C.) and under pressure, or with water added with carboxylic acids such as, for example, acetic acid, used as catalysts of the hydrolysis reaction (U.S. Pat. No. 6,103, 930).

Owing to the variable nature of the impurities present in the articles (colourings, contaminants, etc.), and to the different sources from which the articles come, in order to produce terephthalic acid which is usable in the preparation of resins that can produce articles with acceptable colour characteristics, treatments for the purification of the raw terephthalic acid, such as catalytic combustion of the impurities present and subsequent catalytic hydrogenation, are required (U.S. Pat. No. 5,414,113).

DESCRIPTION OF THE INVENTION

It has unexpectedly been found that it is possible to produce dicarboxylic aromatic acids, in particular terephthalic acid, of sufficient purity and with satisfactory colour characteristics, from manufactured articles for recycling which are made of or contain aromatic polyester resins, in particular PET and ethylene terephthalic copolymers containing up to 20% in moles of isophthalic acid and/or 2,6-naphthalene dicarboxylic acid units, by reaction, at temperatures between 160° and 250° C., of the articles, suitably broken up into chip or fragment form, in solution in a carboxylic acid with 2–6 carbon atoms and with a pKa from 4 to 6, preferably glacial acetic acid, in the presence of catalytic quantities of a strong inorganic or organic acid with a pKa of less than 1, preferably aqueous concentrated hydrochloric acid or concentrated sulphuric acid. It is also possible to operate with anhydrous, gaseous hydrochloric acid (hydrogen chloride) or with fuming sulphuric acid.

Inorganic acids are preferred. The quantity by weight of the acids is generally from 0.5 to 50% by weight relative to the resin, preferably from 1 to 20% by weight.

Water may be present in quantities up to approximately 200% by weight relative to the strong acid.

Hydrochloric acid is preferably used in 20–37% by weight aqueous solution. Sulphuric acid is used concentrated at 96%, or else diluted with water.

The reaction is carried out in an autoclave under autogenous pressure. For example, autoclaves made of stainless steel coated internally with Teflon, or of titanium, may be used.

The reaction temperature is preferably from 180° to 230° C.

The carboxylic acid with 2–6 carbon atoms, preferably glacial acetic acid or glycolic acid, is used in quantities sufficient to solubilize the resin under the reaction conditions; for example, from 2 to 10 parts of acid per part by weight of resin are used.

The article is broken up to produce chips or fragments, for example having for length and/or width dimensions of from 1 to 2 cm. The articles may be coloured or transparent and may contain contaminants, and the fragments may be produced from mixtures of articles of different colours and different origin.

It is also possible to use articles made of or containing polyester resin mixed with polyamides such as, for example, poly(m.xylilene adipamide) or other polymers, in particular, in the form of multi-layer films or of multi-layer bottles in which at least one layer is made of co(polyalkylene terephthalate) and one layer is made of poly(m.xylilene adipamide), or mixtures thereof with polyalkylene terephthalate.

In the case of articles made of blends of polyesters with polyamides, the polyamide dissolves in the reaction medium and does not therefore interfere with the recovery of the dicarboxylic aromatic acid which is present as solid phase.

The reaction is preferably carried out in the absence of oxygen; this is to prevent undesired oxidation reactions.

Upon completion of the reaction (the time is generally a few hours), the autoclave is cooled to bring it to atmospheric pressure. The dicarboxylic acid is separated from the liquid phase by conventional methods, for example, by filtration.

The crude acid may be purified by hot treatment with glacial acetic acid, for example, operating at the reaction temperature.

When terephthalic acid is produced with the use of aqueous hydrochloric acid as the catalyst, a product with a purity of more than 98%, after purification, is obtained.

When the acid is produced with the use of sulphuric acid as the catalyst, the crude acid already has a purity of 97–98%.

In this case, the acid has a grey colouration due to carbon impurities dispersed uniformly in the body of the acid.

Terephthalic acid coloured in this way is suitable for the preparation of resins for bottles by injection blow-moulding, since the parisons produced using this resin dissipate heat easily, thus facilitating the bottle-production cycle.

The grey coloured bottles thus produced are commercially acceptable.

The L colour parameters of the crude terephthalic acid produced with the use of sulphuric acid as the catalyst are between 20 and 80.

The aromatic dicarboxylic acids obtainable according to the process of the present invention, particular reference is made to terephthalic acid, are free from metal compounds deriving from the polycondensation and/or transesterification catalyst used for preparing the polyester resins, in particular are free from antimony compounds.

The method according to the present invention may be performed continuously by recycling of the carboxylic acid after it has been made up with fresh acid and recovery of the acid removed by distillation.

Using acetic acid in for the recovery of terephthalic acid from PET, ethylene glycol monoacetate and diacetate are formed as by-products and are recovered.

The following examples are provided by way of non-limiting illustration of the invention.

EXAMPLE 1

60 ml of glacial acetic acid, 7.5 ml of 20% by weight hydrochloric acid, and 6 g of chips produced by fragmenting PET bottles of various colours were placed in a stainless steel autoclave of 125 ml capacity, coated internally with Teflon.

The autoclave was heated to 200° C. and kept at that temperature for 4 hours.

The autoclave was then cooled to room temperature.

The reaction mixture obtained comprised a white crystalline phase which, upon analysis, after separation by filtration, was found to be formed of terephthalic acid with purity of 83% and with colour parameters of L 72.8, a −1.25, and b 2.51.

The solid thus obtained was purified by treatment in autoclave at 200° C. for 4 h with 60 ml of acetic acid.

4.36 g of terephthalic acid with a purity of 98.2% and with colour parameters of L 82.39, a −2.07, and b 3,51 was obtained.

The yield of terephthalic acid with a purity of 98.2% was 84%.

57 ml of acetic acid with a purity of 90% was recovered from the liquid layer of the reaction mixture by distillation.

EXAMPLE 2

The preparation of Example 1 was repeated, with the sole difference that 1 ml of 96% sulphuric acid was used, operating at 220° C.

The solid reaction product was of a greyish colour and was constituted by terephthalic acid with a purity of 98% and colour parameters of L 47.7, a 1.14, and b 7.74.

The yield of 98% terephthalic acid was 83.3%.

EXAMPLE 3

The preparation of Example 2 was repeated, with the sole difference that 0.5 ml of 96% sulphuric acid was used.

The yield of terephthalic acid with a purity of 97% was 85.2% and the colour parameters of the acid were L 26.7, a 0.70, and b 5.42.

EXAMPLE 4

The preparation of Example 2 was repeated, with the sole difference that 5 ml of distilled water were used, in addition.

An 82.7% yield of terephthalic acid with a purity of 98% was obtained, with colour parameters of L 4.09, a 0.61 and b 8.27.

EXAMPLE 5

The preparation of Example 2 was repeated, with the sole difference that 0.2 ml of fuming sulphuric acid was used.

An 82% yield of terephthalic acid with a purity of 97% was obtained with an L colour parameter of 55.

EXAMPLE 6

The preparation of Example 1 was repeated, with the sole difference that 2 g of anhydrous gaseous hydrochloric acid were introduced into the autoclave.

An 85% yield of terephthalic acid with a purity of 98% was obtained (after purification in acetic acid at 180° C.) with colour parameters of L 83.4, a −2.1, and b 2.5.

Comparison Example 1

The preparation of Example 2 was repeated, with the sole difference that no sulphuric acid was used, but 5 ml of distilled water was used instead.

Terephthalic acid with a purity of 30.0% with a yield of 67.3% and with colour parameters of L 77.0, a −2.73 and b 5.20, was obtained.

Comparison Example 2

The preparation of Example 1 was repeated, with the sole difference that 2.5% by weight of phosphoric acid, relative to the PET chips, was used.

A cloudy solution was obtained.

Comparison Example 3

The preparation of Example 1 was repeated, with the sole difference that hydrochloric acid was not used.

There was no reaction.

EXAMPLE 7

The preparation of Example 2 was repeated, with the sole difference that it was performed at 180° C.

Terephthalic acid with a purity of 97%, with a yield of 83%, and with colour parameters of L 65, a 1.5 and b 5.6 was obtained.

What is claimed is:

1. A method of recovering aromatic discarboxylic acids from manufactured articles for recycling made of or containing aromatic polyester resins, comprising the reaction, at temperatures from between 160° to 250° C., of the article, reduced to chip form, in solution in a carboxylic acid with 2–6 carbon atoms and with a pKa of from 4 to 6, in the presence of catalytic quantities of a strong inorganic or organic acid or mixtures thereof, with a pKa of less than 1 and in which water is present in the reaction mixture in quantities of up to 200% by weight relative to the strong acid.

2. A method according to claim 1, which the carboxylic acid is acetic acid and the strong acid is selected from aqueous hydrochloric acid in concentrations from 20 to 37% by weight, anhydrous gaseous hydrochloric acid, and 96% sulphuric acid.

3. A method according to claim 1 which the strong acid is fuming sulphuric acid.

4. A method of recovering aromatic dicarboxylic acids from manufactured articles for recycling made of or containing aromatic polyester resins, comprising the reaction, at temperatures from between 160° to 250° C., of the article, reduced to chip form, in solution in a carboxylic acid with 2–6 carbon atoms and with a pKa of from 4 to 6, in the presence of catalytic quantities of a strong inorganic or organic acid or mixtures thereof, with a pKa of less than 1, wherein the terephthalic acid is recovered from articles which are made of or contain mixtures of co(polyalkylene terephthalates) with poly(m.xylilene adipamide).

5. A method according to claim 4 in which the terephthalic acid is recovered from articles in the form of multi-layer bottles in which at least one layer of which is made of co(polyalkylene terephthalates) and one layer is made of poly(m.xylilene adipamide) or of mixtures of poly(m.xylilene adipamide) with co(polyalkylene terephthalates).

6. A method according to claim 2 in which terephthalic acid is recovered from articles for recycling, made of or containing polyethylene terephthalate or copolyethylene terephthalate in which up to 20% by weight of the units derived from terephthalic acid are replaced by units derived from isophthalic acid and/or naphthalene discarboxylic acids.

7. A method according to claim 3 in which terephthalic acid is recovered from articles for recycling, made of or containing polyethylene terephthalate or copolyethylene terephthalate in which up to 20% by weight of the units derived from terephthalic acid are replaced by units derived from isophthalic acid and/or naphthalene discarboxylic acids.

8. A method according to claim 1 in which terephthalic acid is recovered from articles for recycling, made of or containing polyethylene terephthalate or copolyethylene terephthalate in which up to 20% by weight of the units derived from terephthalic acid are replaced by units derived from isophthalic acid and/or naphthalene discarboxylic acids.

9. A method according to claim 2 in which the terephthalic acid is recovered from articles which are made of or contain mixtures of co(polyalkylene terephthalates) with poly(m.xylilene adipamide).

10. A method according to claim 3 in which the terephthalic acid is recovered from articles which are made of or contain mixtures of co(polyalkylene terephthalates) with poly(m.xylilene adipamide).

11. A method according to claim 4 in which the carboxylic acid is acetic acid and the strong acid is selected from aqueous hydrochloric acid in concentrations from 20 to 37% by weight, anhydrous gaseous hydrochloric acid, and 96% sulphuric acid up to 96% sulphuric acid.

12. A method according to claim 4 in which the strong acid is fuming sulphuric acid.

13. A method according to claim 4 in which water is present in the reaction mixture in quantities up to 200% by weight relative to the strong acid.

14. A method according to claim 4 in which terephthalic acid is recovered from articles which are made of or containing polyethylene terephthalate or copolyethylene terephthalate in which up to 20% by weight of the units derived from terephthalic acid are replaced by units derived from isophthalic acid and/or naphthalene discarboxylic acids.

15. A method of recovering aromatic dicarboxylic acids from manufactured articles for recycling made of or containing aromatic polyester resins, comprising the reaction, at temperatures from between 160° to 250° C. and in the absence of oxygen, of the article, reduced to chip form, in solution in a carboxylic acid with 2–6 carbon atoms and with a pKa of from 4 to 6, in the presence of catalytic quantities of a strong inorganic or organic acid or mixtures thereof, with a pKa of less than 1.

16. A method according to claim 15 in which the carboxylic acid is acetic acid and the strong acid is selected from aqueous hydrochloric acid in concentrations from 20 to 37% by weight, anhydrous gaseous hydrochloric acid, and 96% sulphuric acid.

17. A method according to claim 15 in which the strong acid is fuming sulphuric acid.

18. A method according to claim 15 in which terephthalic acid is recovered from articles for recycling, made of or containing polyethylene terephthalate or copolyethylene terephthalate in which up to 20% by weight of the units derived from terephthalic acid are replaced by units derived from isophthalic acid and/or naphthalene discarboxylic acids.

19. A method according to claim 15 in which water is present in the reaction mixture in quantities of up to 200% by weight relative to the strong acid.

20. A method according to claim 16 in which water is present in the reaction mixture in quantities of up to 200% by weight relative to the strong acid.

21. A method according to claim 17 in which water is present in the reaction mixture in quantities of up to 200% by weight relative to the strong acid.

22. A method according to claim 16 in which terephthalic acid is recovered from articles for recycling, made of or containing polyethylene terephthalate or copolyethylene terephthalate in which up to 20% by weight of the units derived from terephthalic acid are replaced by units derived from isophthalic acid and/or naphthalene dicarboxylic acids.

23. A method according to claim 17 in which terephthalic acid is recovered from articles for recycling, made of or containing polyethylene terephthalate or copolyethylene terephthalate in which up to 20% by weight of the units derived from terephthalic acid are replaced by units derived from isophthalic acid and/or naphthalene dicarboxylic acids.

24. A method according to claim 18 in which terephthalic acid is recovered from articles for recycling, made of or containing polyethylene terephthalate or copolyethylene terephthalate in which up to 20% by weight of the units derived from terephthalic acid are replaced by units derived from isophthalic acid and/or naphthalene dicarboxylic acids.

\* \* \* \* \*